United States Patent
Matheny

(10) Patent No.: US 9,737,569 B2
(45) Date of Patent: *Aug. 22, 2017

(54) COMPOSITIONS AND METHODS FOR TREATMENT OF CARDIOVASCULAR DISORDERS

(71) Applicant: CorMatrix Cardiovascular, Inc., Roswell, GA (US)

(72) Inventor: Robert G Matheny, Norcross, GA (US)

(73) Assignee: CorMatrix Cardiovascular, Inc., Roswell, GA (US)

( * ) Notice: Subject to any disclaimer, the term of this patent is extended or adjusted under 35 U.S.C. 154(b) by 58 days.

This patent is subject to a terminal disclaimer.

(21) Appl. No.: 14/644,476

(22) Filed: Mar. 11, 2015

(65) Prior Publication Data

US 2015/0182662 A1  Jul. 2, 2015

Related U.S. Application Data

(63) Continuation of application No. 13/782,115, filed on Mar. 1, 2013, and a continuation-in-part of application No. 13/573,569, filed on Sep. 24, 2012, and a continuation-in-part of application No. 11/334,631, filed on Jan. 18, 2006.

(51) Int. Cl.

| | |
|---|---|
| *A61K 35/35* | (2015.01) |
| *A61K 45/06* | (2006.01) |
| *A61K 35/12* | (2015.01) |
| *A61L 27/36* | (2006.01) |
| *A61K 48/00* | (2006.01) |
| *A61K 38/18* | (2006.01) |
| *A61L 27/38* | (2006.01) |
| *A61L 27/54* | (2006.01) |
| *A61M 1/12* | (2006.01) |

(52) U.S. Cl.

CPC ............. *A61K 35/35* (2013.01); *A61K 35/12* (2013.01); *A61K 38/18* (2013.01); *A61K 38/185* (2013.01); *A61K 38/1808* (2013.01); *A61K 38/1841* (2013.01); *A61K 38/1866* (2013.01); *A61K 45/06* (2013.01); *A61K 48/00* (2013.01); *A61L 27/3604* (2013.01); *A61L 27/367* (2013.01); *A61L 27/3629* (2013.01); *A61L 27/3633* (2013.01); *A61L 27/3826* (2013.01); *A61L 27/3834* (2013.01); *A61L 27/54* (2013.01); *A61M 1/122* (2014.02); *A61L 2300/414* (2013.01); *A61L 2300/434* (2013.01); *A61L 2300/64* (2013.01); *A61L 2430/20* (2013.01); *A61M 2205/05* (2013.01)

(58) Field of Classification Search

USPC .................. 424/484, 423, 520, 583; 435/378

See application file for complete search history.

(56) References Cited

U.S. PATENT DOCUMENTS

| | | | | |
|---|---|---|---|---|
| 2010/0047351 | A1* | 2/2010 | Zeitlin | A61K 35/50 424/484 |
| 2011/0195107 | A1* | 8/2011 | Min | A61L 27/3604 424/423 |
| 2011/0250182 | A1* | 10/2011 | Abbot | A61K 35/28 424/93.7 |

OTHER PUBLICATIONS

Snider et al Circ Res. Apr. 11, 2008;102(7):752-60 Periostin is required for maturation and extracellular matrix stabilization of noncardiomyocyte lineages of the heart.*
Hoshiba et al 2010 Decellularized matrices for tissue engineering Expert Opinion on Biological Therapy 1744-7682.*
Duan-Arnold et al., Angiogenic Potential of Cryopreserved AmnioticMembrane Is Enhanced Through Retention of All Tissue Components in Their Native State Advances in Wound Care, vol. 4, No. 9 513-522.*
Niknejad et al., Properties of the Amniotic Membrane for Potential Use in Tissue Engineering European Cells and Materials, 2008, pp. 88-99.*

* cited by examiner

Primary Examiner — Maria Leavitt
(74) Attorney, Agent, or Firm — Francis Law Group

(57) ABSTRACT

ECM based compositions including amniotic membrane and methods for employing same to treat cardiovascular disorders.

2 Claims, 2 Drawing Sheets

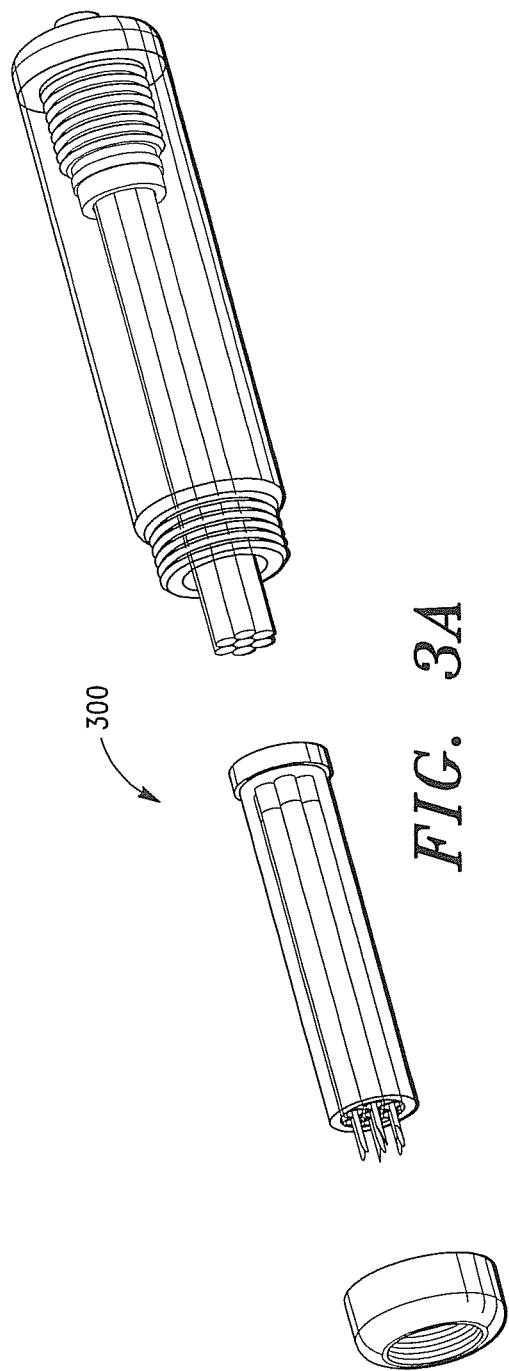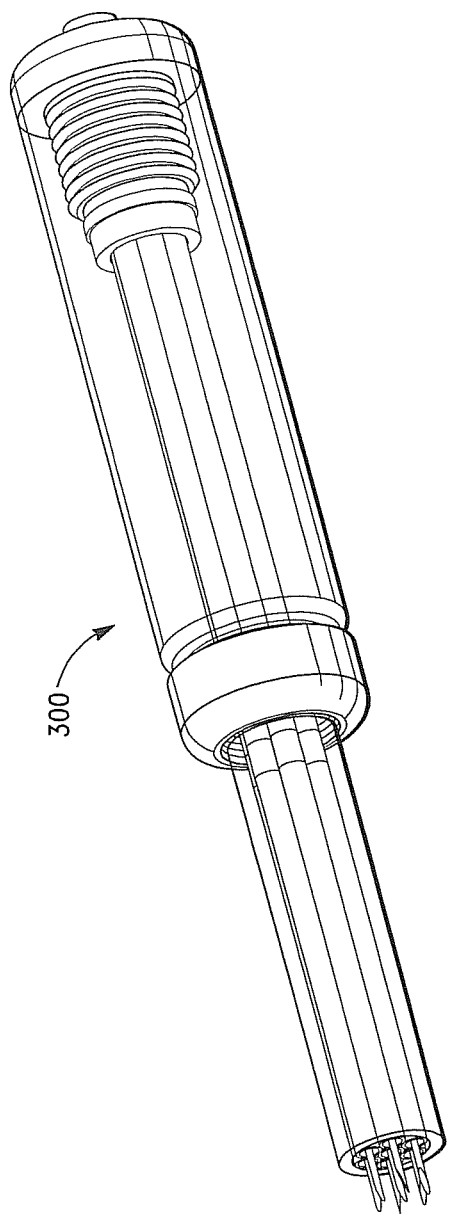

COMPOSITIONS AND METHODS FOR TREATMENT OF CARDIOVASCULAR DISORDERS

CROSS-REFERENCES TO RELATED APPLICATIONS

This application is a continuation of U.S. application Ser. No. 13/782,115, filed on Mar. 1, 2013, now U.S. Pat. No. 9,119,899, which is a continuation-in-part of U.S. application Ser. No. 13/573,569, filed on Sep. 24, 2012, now U.S. Pat. No. 9,072,816, which is a continuation-in-part of U.S. application Ser. No. 13/328,287, filed on Dec. 16, 2011, which claims the benefit of U.S. provisional Application No. 61/425,287, filed on Dec. 20, 2010.

FIELD OF THE INVENTION

The present invention relates to methods for treating cardiovascular disorders. More particularly, the present invention relates to extracellular matrix (ECM) compositions and methods for treating cardiovascular disorders.

BACKGROUND OF THE INVENTION

As is well known in the art, heart failure can be caused by a diverse array of cardiovascular disorders that reduce the efficiency of the myocardium, including ischemic heart disease, coronary artery disease, and a defective or diseased heart valve. Among the noted disorders, ischemic heart disease, which commonly presents as a myocardial infarction, is the leading cause of heart failure.

Indeed, in 2004 alone, the World Health Organization estimated that 12.2% of worldwide deaths occurred as a result of ischemic heart disease. Ischemic heart disease was also deemed the leading cause of death in middle to high income countries and second only to respiratory infections in lower income countries. *The Global Burden of Disease: World Health Organization* 2004 *Update*, Geneva (2008). Worldwide more than 3 million people present with a ST elevation myocardial infarction (STEMI) and 4 million people present with a non-ST elevation myocardial infarction (NSTEMI) a year. White, et al., *Acute Myocardial Infarction,* Lancet 372 (9638), pp. 570-84 (August 2008).

Rates of death from ischemic heart disease have slowed or declined in most high income countries, although cardiovascular disease still accounted for 1 in 3 of all deaths in the USA in 2008. Roger, et al., *Executive summary: Heart Disease and Stroke Statistics*-2012 *update: A report from the American Heart Association,* Circulation 125 (1), pp. 188-97 (January 2012).

In contrast, ischemic heart disease is becoming a more common cause of death in the developing world. For example in India, ischemic heart disease had become the leading cause of death by 2004; accounting for 1.46 million deaths (14% of total deaths). Deaths in India due to ischemic heart disease were also expected to double during 1985-2015. Gupta, et al., *Epidemiology and Causation of Coronary Heart Disease and Stroke in India,* Heart 94 (1), pp. 16-26 (January 2008).

Globally, it is predicted that disability adjusted life years (DALYs) lost to ischemic heart disease will account for 5.5% of total DALYs in 2030, making it the second most important cause of disability (after unipolar depressive disorder), as well as the leading cause of death by this date.

Ischemic heart disease often occurs when myocardial tissue is no longer receiving adequate blood flow. Various methods for treating ischemic heart disease have thus been developed. Such methods include systemic delivery of various pharmacological agents.

Several additional methods for treating ischemic heart disease are directed to re-establishing blood flow to the ischemic area. Such methods include stimulation of angiogenesis and surgical intervention, e.g. bypass surgery or angioplasty. Other methods include the use of lasers to bore holes through the ischemic area(s) to promote blood flow. As one can readily appreciate, there are numerous incumbent risks associated with the noted methods.

A further method for treating ischemic heart disease is the direct delivery of bioactive or pharmacological agents to the ischemic area. Illustrative is the delivery of extracellular matrix (ECM) based compositions directly to cardiovascular tissue disclosed in Co-pending application Ser. No. 13/573,569.

More recently, ventricular assist devices (VADs) have been employed as treatment platforms for various pharmacological therapies, e.g. stem cell administration, which have been developed to treat cardiovascular disorders, including ischemic heart disease. VADs are designed to support (or augment) the function of either the right (RVAD) or left (LVAD) ventricle, or both at once (BiVAD). The type of VAD employed depends primarily on the underlying cardiovascular disorder, and the pulmonary arterial resistance that determines the load on the right ventricle.

Although the direct delivery of bioactive or pharmacological agents; particularly, the ECM based compositions disclosed in Co-pending application Ser. No. 13/573,569, and other treatment therapies employing ventricular assistance have been found effective to treat cardiovascular disorders and, thereby, heart failure, there remains a need to provide even more effective means for treating cardiovascular disorders.

It is therefore an object of the present invention to provide improved compositions and methods for treating damaged or diseased biological tissue; particularly, cardiovascular tissue and, hence, cardiovascular disorders associated therewith.

It is another object of the present invention to provide ECM based compositions comprising amniotic membrane for treating damaged or diseased biological tissue.

It is another an object of the present invention to provide ECM based compositions that promote tissue survival, and induce neovascularization and regeneration of damaged cardiovascular tissue.

It is yet another object of the present invention to provide methods for treating cardiovascular disorders that includes administration of an ECM based composition, which, when delivered to damaged biological tissue; particularly, cardiovascular tissue, induces neovascularization, host tissue proliferation, bioremodeling, and regeneration of cardiovascular tissue and associated structures with site-specific structural and functional properties.

SUMMARY OF THE INVENTION

The present invention is directed to ECM based compositions and methods for treating damaged or diseased biological tissue.

In a preferred embodiment of the invention, the ECM based compositions comprise amniotic membrane.

In some embodiments, the ECM based compositions further include at least one additional biologically active agent that supports the treatment of damaged cardiovascular tissue and/or bioremodeling and/or regeneration of tissue.

In some embodiments of the invention, the biologically active agent comprises a growth factor selected from the group comprising transforming growth factor-alpha (TGF-α), transforming growth factor-beta (TGF-β), fibroblast growth factor-2 (FGF-2), basic fibroblast growth factor (bFGF) and vascular epithelial growth factor (VEGF).

In some embodiments of the invention, the biologically active agent comprises a cell selected from the group comprising human embryonic stem cells, fetal cardiomyocytes, myofibroblasts, and mesenchymal stem cells.

In some embodiments of the invention, the biologically active agent comprises a protein selected from the group comprising proteoglycans, glycosaminoglycans (GAGs), glycoproteins and cytokines.

In some embodiments, the ECM based compositions further include at least one pharmacological agent.

In some embodiments of the invention, the pharmacological agent comprises an antiarrhythmic agent selected from the group comprising quinidine, procainamide, disopyramide, lidocaine, phenytoin, mexiletine, flecainide, propafenone, moricizine, propranolol, esmolol, timolol, metoprolol, atenolol, amiodarone, sotalol, ibutilide, dofetilide, verapamil, diltiazem, adenosine and digoxin.

In some embodiments of the invention, the pharmacological agent comprises an anti-inflammatory agent or composition.

In some embodiments of the invention, the biologically active component comprises a statin selected from the group comprising atorvastatin, cerivastatin, fluvastatin, lovastatin, mevastatin, pitavastatin, pravastatin, rosuvastatin, and simvastatin.

In some embodiments of the invention, the ECM based compositions are formulated to facilitate injection of the ECM based compositions to damaged or diseased tissue (i.e. injectable compositions).

In some embodiments of the invention, ECM based compositions are in the form of a graft.

BRIEF DESCRIPTION OF THE DRAWINGS

Further features and advantages will become apparent from the following and more particular description of the preferred embodiments of the invention, as illustrated in the accompanying drawings, and in which like referenced characters generally refer to the same parts or elements throughout the views, and in which:

FIG. 3A is an exploded perspective view of one embodiment of a multi-needle injection apparatus that is suitable for direct administration of ECM compositions to biological tissue, e.g. cardiovascular tissue, in accordance with the invention; and FIG. 3B is an assembled perspective view of the multi-needle injection apparatus shown in FIG. 3A, in accordance with the invention.

DETAILED DESCRIPTION OF THE PREFERRED EMBODIMENT

Figure 1:
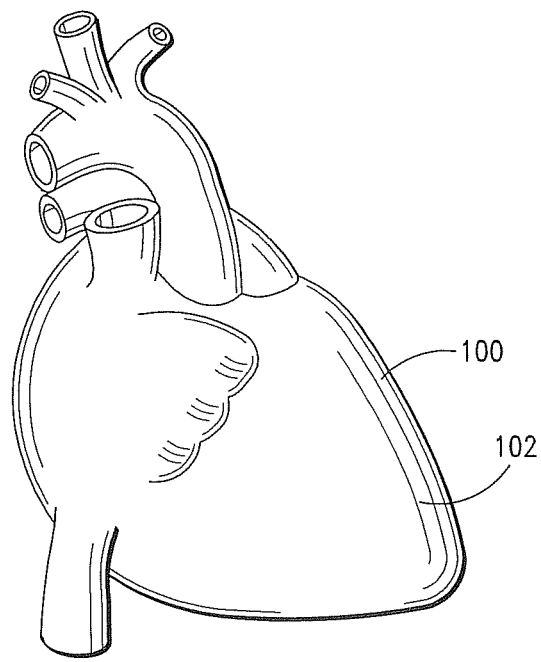
FIG. 1 is a depiction of a normal heart.

Before describing the present invention in detail, it is to be understood that this invention is not limited to particularly exemplified apparatus, systems, compositions or methods as such may, of course, vary. Thus, although a number of systems, compositions and methods similar or equivalent to those described herein can be used in the practice of the present invention, the preferred systems, compositions and methods are described herein.

It is also to be understood that, although a preferred method of delivering an ECM based composition of the invention to biological tissue comprises direct injection into the tissue. The delivery of an ECM based composition is not limited to direct injection. According to the invention, an ECM based composition of the invention can be delivered to biological tissue by other conventional means, including topical administration.

It is further to be understood that the terminology used herein is for the purpose of describing particular embodiments of the invention only and is not intended to be limiting.

Unless defined otherwise, all technical and scientific terms used herein have the same meaning as commonly understood by one having ordinary skill in the art to which the invention pertains.

Further, all publications, patents and patent applications cited herein, whether supra or infra, are hereby incorporated by reference in their entirety.

Finally, as used in this specification and the appended claims, the singular forms "a, "an" and "the" include plural referents unless the content clearly dictates otherwise. Thus, for example, reference to "an anti-inflammatory" includes two or more such agents and the like.

Definitions

The terms "cardiovascular disorder" and "heart failure" are used interchangeably herein, and mean and include any abnormal function of the heart; particularly, abnormal functions or deficiency of the myocardium. The terms "cardiovascular disorder" and "heart failure" thus include, without limitation, ischemic heart disease, coronary artery disease, a defective or diseased heart valve, myocarditis, an inflammatory disease, cardiomyopathy and amyloidosis.

The terms "cardiovascular tissue damage," "cardiac tissue damage," and "cardiac tissue injury" and are used interchangeably herein, and mean and include any area of abnormal tissue in the cardiovascular system or heart caused by a disease, disorder, injury or damage, including damage to the epicardium, endocardium and/or myocardium.

As is well known in the art, cardiovascular tissue damage most often involves damage or injury to the myocardium and, therefore, for the purposes of this disclosure, myocardial damage or injury is equivalent to cardiovascular tissue damage.

The terms "extracellular matrix", "ECM" and "ECM material" are used interchangeably herein, and mean and include a collagen-rich substance that is found in between cells in mammalian tissue, and any material processed therefrom, e.g. decellularized ECM. According to the invention, ECM can be derived from a variety of mammalian tissue sources, including, without limitation, small intestine submucosa (SIS), urinary bladder submucosa (UBS), stomach submucosa (SS), central nervous system tissue, epithelium of mesodermal origin, i.e. mesothelial tissue, dermal extracellular matrix, subcutaneous extracellular matrix, gastrointestinal extracellular matrix, i.e. large and small intestines, tissue surrounding growing bone, placental extracellular matrix, omentum extracellular matrix, cardiac extracellular matrix, e.g., pericardium and/or myocardium, kidney extracellular matrix, pancreas extracellular matrix, lung extracellular matrix, and combinations thereof. The ECM material can also comprise collagen from mammalian sources.

ECM can also be derived from basement membrane of mammalian tissue/organs, including, without limitation, urinary basement membrane (UBM), liver basement membrane (LBM), and amnion, chorion, allograft pericardium, allograft acellular dermis, amniotic membrane, Wharton's jelly, and combinations thereof.

The term "chamber remodeling", as used herein, means and includes a series of events (which may include changes in gene expression, molecular, cellular and interstitial changes) that result in changes in size, shape and function of biological tissue following stress or injury. As is well known in the art, remodeling can occur after a myocardial infarction, pressure overload (e.g., aortic stenosis, hypertension), volume overload (e.g., valvular regurgitation), inflammatory heart disease (e.g., myocarditis), or in idiopathic cases (e.g., idiopathic dilated cardiomyopathy).

The term "angiogenesis", as used herein, means a physiologic process involving the growth of new blood vessels from pre-existing blood vessels.

The term "neovascularization", as used herein, means and includes the formation of functional vascular networks that can be perfused by blood or blood components. Neovascularization includes angiogenesis, budding angiogenesis, intussuceptive angiogenesis, sprouting angiogenesis, therapeutic angiogenesis and vasculogenesis.

The terms "pharmacological agent", "pharmacological composition" and "biologically active agent", as used herein, mean and include an agent, drug, compound, composition of matter or mixture thereof, including its formulation, which provides some therapeutic, often beneficial, effect. This includes any physiologically or pharmacologically active substance that produces a localized or systemic effect or effects in animals, including warm blooded mammals, humans and primates; avians; domestic household or farm animals, such as cats, dogs, sheep, goats, cattle, horses and pigs; laboratory animals, such as mice, rats and guinea pigs; fish; reptiles; zoo and wild animals; and the like.

The terms "pharmacological agent" and "biologically active agent" thus mean and include, without limitation, antibiotics, anti-arrhythmic agents, anti-viral agents, analgesics, steroidal anti-inflammatories, non-steroidal anti-inflammatories, anti-neoplastics, anti-spasmodics, modulators of cell-extracellular matrix interactions, proteins, hormones, growth factors, matrix metalloproteinases (MMPS), enzymes and enzyme inhibitors, anticoagulants and/or anti-thrombic agents, DNA, RNA, modified DNA and RNA, NSAIDs, inhibitors of DNA, RNA or protein synthesis, polypeptides, oligonucleotides, polynucleotides, nucleoproteins, compounds modulating cell migration, compounds modulating proliferation and growth of tissue, and vasodilating agents.

The terms "pharmacological agent" and "biologically active agent" accordingly include, without limitation, atropine, tropicamide, dexamethasone, dexamethasone phosphate, betamethasone, betamethasone phosphate, prednisolone, triamcinolone, triamcinolone acetonide, fluocinolone acetonide, anecortave acetate, budesonide, cyclosporine, FK-506, rapamycin, ruboxistaurin, midostaurin, flurbiprofen, suprofen, ketoprofen, diclofenac, ketorolac, nepafenac, lidocaine, neomycin, polymyxin b, bacitracin, gramicidin, gentamicin, oyxtetracycline, ciprofloxacin, ofloxacin, tobramycin, amikacin, vancomycin, cefazolin, ticarcillin, chloramphenicol, miconazole, itraconazole, trifluridine, vidarabine, ganciclovir, acyclovir, cidofovir, ara-amp, foscarnet, idoxuridine, adefovir dipivoxil, methotrexate, carboplatin, phenylephrine, epinephrine, dipivefrin, timolol, 6-hydroxydopamine, betaxolol, pilocarpine, carbachol, physostigmine, demecarium, dorzolamide, brinzolamide, latanoprost, sodium hyaluronate, insulin, verteporfin, pegaptanib, ranibizumab, and other antibodies, antineoplastics, Anti VGEFs, ciliary neurotrophic factor, brain-derived neurotrophic factor, bFGF, Caspase-1 inhibitors, Caspase-3 inhibitors, α-Adrenoceptors agonists, NMDA antagonists, Glial cell line-derived neurotrophic factors (GDNF), pigment epithelium-derived factor (PEDF), and NT-3, NT-4, NGF, IGF-2.

According to the invention, the terms "pharmacological agent" and "biologically active agent" further include, without limitation, the following growth factors: platelet derived growth factor (PDGF), epidermal growth factor (EGF), transforming growth factor alpha (TGF-alpha), transforming growth factor beta (TGF-beta), fibroblast growth factor-2 (FGF-2), basic fibroblast growth factor (bFGF), vascular epithelial growth factor (VEGF), hepatocyte growth factor (HGF), insulin-like growth factor (IGF), nerve growth factor (NGF), platelet derived growth factor (PDGF), tumor necrosis factor alpha (TNA-alpha), and placental growth factor (PLGF).

The terms "pharmacological agent" and "biologically active agent" further include, without limitation, the following Class I-Class V antiarrhythmic agents: (Class Ia) quinidine, procainamide and disopyramide; (Class Ib) lidocaine, phenytoin and mexiletine; (Class Ic) flecainide, propafenone and moricizine; (Class II) propranolol, esmolol, timolol, metoprolol and atenolol; (Class III) amiodarone, sotalol, ibutilide and dofetilide; (Class IV) verapamil and diltiazem) and (Class V) adenosine and digoxin.

The terms "pharmacological agent" and "biologically active agent" further include, without limitation, the following anti-inflammatories: alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, cicloprofen, cintazone, cliprofen, clobetasol propionate, clobetasone butyrate, clopirac, cloticasone propionate, cormethasone acetate, cortodoxone, decanoate, deflazacort, delatestryl, depo-testosterone, desonide, desoximetasone, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, mesterolone, methandrostenolone, methenolone, methenolone acetate, methylprednisolone suleptanate, momiflumate, nabumetone, nandrolone, naproxen, naproxen sodium, naproxol, nimazone, olsalazine sodium, orgotein, orpanoxin, oxandrolane, oxaprozin, oxyphenbutazone, oxymetholone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, stanozolol, sudoxicam, sulindac, suprofen, talmetacin, talniflumate, talosalate, tebufelone, tenidap, tenidap sodium, tenoxicam, tesicam, tesimide, testosterone, testosterone blends, tetrydamine, tiopinac, tixocortol pivalate, tolmetin, tolmetin sodium, triclonide, triflumidate, zidometacin, and zomepirac sodium.

The term "biologically active agent" further includes, without limitation, organisms that have the potential to induce modulating proliferation, and/or growth and/or regeneration of tissue. The terms "biologically active agent" thus includes, without limitation, the following cells: human embryonic stem cells, fetal cardiomyocytes, myofibroblasts, mesenchymal stem cells, autotransplated expanded cardiomyocytes, adipocytes, totipotent cells, pluripotent cells, blood stem cells, myoblasts, adult stem cells, bone marrow cells, mesenchymal cells, embryonic stem cells, parenchymal cells, epithelial cells, endothelial cells, mesothelial cells, fibroblasts, osteoblasts, chondrocytes, exogenous cells, endogenous cells, stem cells, hematopoietic stem cells, bone-marrow derived progenitor cells, myocardial cells, skeletal cells, fetal cells, undifferentiated cells, multi-potent progenitor cells, unipotent progenitor cells, monocytes, cardiac myoblasts, skeletal myoblasts, macrophages, capillary endothelial cells, xenogenic cells, allogenic cells, and post-natal stem cells.

According to the invention, the terms "pharmacological agent" and "biologically active agent" can further include the following active agents (referred to interchangeably herein as a "protein", "peptide" and "polypeptide"): collagen (types I-V), proteoglycans, glycosaminoglycans (GAGs), glycoproteins, cytokines, cell-surface associated proteins, cell adhesion molecules (CAM), angiogenic growth factors, endothelial ligands, matrikines, cadherins, immuoglobins, fibril collagens, non-fibrallar collagens, basement membrane collagens, multiplexins, small-leucine rich proteoglycans, decorins, biglycans, fibromodulins, keratocans, lumicans, epiphycans, heparin sulfate proteoglycans, perlecans, agrins, testicans, syndecans, glypicans, serglycins, selectins, lecticans, aggrecans, versicans, neurocans, brevicans, cytoplasmic domain-44 (CD-44), macrophage stimulating factors, amyloid precursor proteins, heparins, chondroitin sulfate B (dermatan sulfate), chondroitin sulfate A, heparin sulfates, hyaluronic acids, fibronectins, tenascins, elastins, fibrillins, laminins, nidogen/enactins, fibulin I, finulin II, integrins, transmembrane molecules, thrombospondins, osteopontins, and angiotensin converting enzymes (ACE).

The terms "ECM composition" and "ECM based composition" are used interchangeably herein and mean and include a composition comprising at least one ECM material, and, in some embodiments; preferably amniotic membrane, and/or a "biologically active agent" and/or "pharmacological agent" and/or any additional agent or component identified herein.

The term "therapeutically effective", as used herein, means that the amount of the "ECM composition" and/or "ECM based composition" and/or "biologically active agent" and/or "pharmacological agent" administered is of sufficient quantity to ameliorate one or more causes, symptoms, or sequelae of a disease or disorder. Such amelioration only requires a reduction or alteration, not necessarily elimination, of the cause, symptom, or sequelae of a disease or disorder.

The terms "prevent" and "preventing" are used interchangeably herein, and mean and include reducing the frequency or severity of a disease, condition or disorder. The term does not require an absolute preclusion of the disease, condition or disorder. Rather, this term includes decreasing the chance for disease occurrence.

The terms "treat" and "treatment" are used interchangeably herein, and mean and include medical management of a patient with the intent to cure, ameliorate, stabilize, or prevent a disease, pathological condition or disorder. The terms include "active treatment", i.e. treatment directed specifically toward the improvement of a disease, pathological condition or disorder, and "causal treatment", i.e. treatment directed toward removal of the cause of the associated disease, pathological condition or disorder.

The terms "treat" and "treatment" further include "palliative treatment", i.e. treatment designed for the relief of symptoms rather than the curing of the disease, pathological condition or disorder, "preventative treatment", i.e. treatment directed to minimizing or partially or completely inhibiting the development of the associated disease, pathological condition or disorder, and "supportive treatment", i.e. treatment employed to supplement another specific therapy directed toward the improvement of the associated disease, pathological condition or disorder.

The terms "delivery" and "administration" are used interchangeably herein, and mean and include providing an "ECM composition" or "ECM based composition" to a treatment site, e.g., damaged tissue, through any method appropriate to deliver the functional agent or formulation or composition to the treatment site. Non-limiting examples of delivery methods include direct injection, percutaneous delivery and topical application at the treatment site.

The term "percutaneous", as used herein, means and includes any penetration through the skin of a patient or subject, whether in the form of a small cut, incision, hole, cannula, tubular access sleeve or port or the like.

The terms "patient" and "subject" are used interchangeably herein, and mean and include warm blooded mammals, humans and primates; avians; domestic household or farm animals, such as cats, dogs, sheep, goats, cattle, horses and pigs; laboratory animals, such as mice, rats and guinea pigs; fish; reptiles; zoo and wild animals; and the like.

The term "comprise" and variations of the term, such as "comprising" and "comprises," means "including, but not limited to" and is not intended to exclude, for example, other additives, components, integers or steps.

The following disclosure is provided to further explain in an enabling fashion the best modes of performing one or more embodiments of the present invention. The disclosure is further offered to enhance an understanding and appreciation for the inventive principles and advantages thereof, rather than to limit in any manner the invention. The invention is defined solely by the appended claims including any amendments made during the pendency of this application and all equivalents of those claims as issued.

As indicated above, the present invention is directed to ECM based compositions and methods for treating damaged or diseased biological tissue.

In a preferred embodiment of the invention, the ECM based compositions include at least one extracellular matrix (hereinafter "ECM material").

According to the invention, the ECM material can be derived from various mammalian tissue sources and methods for preparing same, such as disclosed in U.S. Pat. Nos. 7,550,004, 7,244,444, 6,379,710, 6,358,284, 6,206,931, 5,733,337 and 4,902,508 and U.S. application Ser. No.

12/707,427; which are incorporated by reference herein in their entirety. The mammalian tissue sources include, without limitation, small intestine submucosa (SIS), urinary bladder submucosa (UBS), stomach submucosa (SS), central nervous system tissue, epithelium of mesodermal origin, i.e. mesothelial tissue, dermal extracellular matrix, subcutaneous extracellular matrix, gastrointestinal extracellular matrix, i.e. large and small intestines, tissue surrounding growing bone, placental extracellular matrix, ornamentum extracellular matrix, cardiac extracellular matrix, e.g., pericardium and/or myocardium, kidney extracellular matrix, pancreas extracellular matrix, lung extracellular matrix, and combinations thereof. The ECM material can also comprise collagen from mammalian sources.

The ECM material can also be derived from basement membrane of mammalian tissue/organs, including, without limitation, urinary basement membrane (UBM), liver basement membrane (LBM), and amnion, chorion, allograft pericardium, allograft acellular dermis, amniotic membrane, Wharton's jelly, and combinations thereof.

In a preferred embodiment of the invention, the ECM based compositions comprise amniotic membrane.

According to the invention, the ECM based compositions can comprise mixed liquids, mixed emulsions, mixed gels, mixed pastes, or mixed solid particulates. The ECM based compositions can also comprise solid members, such as grafts.

According to the invention, the ECM based compositions of the invention can further include one or more biologically active or pharmacological agents or compositions, which aid in the treatment of damaged tissue and/or facilitate the bioremodeling and/or tissue regeneration process.

In some embodiments of the invention, the biologically active agent comprises a growth factor. According to the invention, suitable growth factors include, without limitation, a platelet derived growth factor (PDGF), epidermal growth factor (EGF), transforming growth factor alpha (TGF-alpha), transforming growth factor beta (TGF-beta), fibroblast growth factor-2 (FGF-2), basic fibroblast growth factor (bFGF), vascular epithelial growth factor (VEGF), hepatocyte growth factor (HGF), insulin-like growth factor (IGF), nerve growth factor (NGF), platelet derived growth factor (PDGF), tumor necrosis factor alpha (TNA-alpha), and placental growth factor (PLGF).

In some embodiments of the invention, the biologically active agent comprises a cell. According to the invention, suitable cells include, without limitation, a human embryonic stem cell, fetal cardiomyocyte, myofibroblast, mesenchymal stem cell, autotransplanted expanded cardiomyocyte, adipocyte, totipotent cell, pluripotent cell, blood stem cell, myoblast, adult stem cell, bone marrow cell, parenchymal cell, epithelial cell, endothelial cell, mesothelial cell, fibroblast, myofibroblast, osteoblast, chondrocyte, exogenous cell, endogenous cell, stem cell, hematopoetic stem cell, bone marrow-derived progenitor cell, progenitor cell, myocardial cell, skeletal cell, undifferentiated cell, multipotent progenitor cell, unipotent progenitor cell, monocyte, cardiomyocyte, skeletal myoblast, macrophage, capillary endothelial cell, xenogenic cell and allogenic cell.

In some embodiments of the invention, the ECM based compositions include a protein. According to the invention, the protein can comprise, without limitation, collagen, proteoglycan, glycosaminoglycan (GAG) chain, glycoprotein, cytokine and cell-surface associated protein, heparin, chondroitin sulfate B (dermatan sulfate), chondroitin sulfate A, heparan sulfate, hyaluronic acid, fibronectin (Fn), tenascin, elastin, fibrillin, laminin, nidogen/entactin, fibulin I and fibulin II.

According to the invention, the pharmacological agents (or compositions) can comprise, without limitation, antiarrhythmic agents, antibiotics or antifungal agents, anti-viral agents, anti-pain agents, anesthetics, analgesics, steroidal anti-inflammatories, non-steroidal anti-inflammatories, antineoplastics, anti-spasmodics, modulators of cell-extracellular matrix interactions, proteins, hormones, enzymes and enzyme inhibitors, anticoagulants and/or antithrombic agents, DNA, RNA, modified DNA and RNA, NSAIDs, inhibitors of DNA, RNA or protein synthesis, polypeptides, oligonucleotides, polynucleotides, nucleoproteins, compounds modulating cell migration, compounds modulating proliferation and growth of tissue, and vasodilating agents.

Suitable pharmacological agents and/or compositions accordingly include, without limitation, atropine, tropicamide, dexamethasone, dexamethasone phosphate, betamethasone, betamethasone phosphate, prednisolone, triamcinolone, triamcinolone acetonide, fluocinolone acetonide, anecortave acetate, budesonide, cyclosporine, FK-506, rapamycin, ruboxistaurin, midostaurin, flurbiprofen, suprofen, ketoprofen, diclofenac, ketorolac, nepafenac, lidocaine, neomycin, polymyxin b, bacitracin, gramicidin, gentamicin, oyxtetracycline, ciprofloxacin, ofloxacin, tobramycin, amikacin, vancomycin, cefazolin, ticarcillin, chloramphenicol, miconazole, itraconazole, trifluridine, vidarabine, ganciclovir, acyclovir, cidofovir, ara-amp, foscarnet, idoxuridine, adefovir dipivoxil, methotrexate, carboplatin, phenylephrine, epinephrine, dipivefrin, timolol, 6-hydroxydopamine, betaxolol, pilocarpine, carbachol, physostigmine, demecarium, dorzolamide, brinzolamide, latanoprost, sodium hyaluronate, insulin, verteporfin, pegaptanib, ranibizumab, and other antibodies, antineoplastics, Anti VGEFs, ciliary neurotrophic factor, brain-derived neurotrophic factor, bFGF, Caspase-1 inhibitors, Caspase-3 inhibitors, α-Adrenoceptors agonists, NMDA antagonists, Glial cell line-derived neurotrophic factors (GDNF), pigment epithelium-derived factor (PEDF), and NT-3, NT-4, NGF, IGF-2.

In some embodiments of the invention, the pharmacological agent comprises an antiarrhythmic agent selected from the group comprising, without limitation, quinidine, procainamide, disopyramide, lidocaine, phenytoin, mexiletine, flecainide, propafenone, moricizine, propranolol, esmolol, timolol, metoprolol, atenolol, amiodarone, sotalol, ibutilide, dofetilide, verapamil, diltiazem, adenosine and digoxin.

In some embodiments of the invention, the pharmacological agent comprises an anti-inflammatory agent selected from the group comprising, without limitation, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, cicloprofen, cintazone, cliprofen, clobetasol propionate, clobetasone butyrate, clopirac, cloticasone propionate, cormethasone acetate, cortodoxone, decanoate, deflazacort, delatestryl, depo-testosterone, desonide, desoximetasone, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, mesterolone, methandrostenolone, methenolone, methenolone acetate, methylprednisolone suleptanate, momiflumate, nabumetone, nandrolone, naproxen, naproxen sodium, naproxol, nimazone, olsalazine sodium, orgotein, orpanoxin, oxandrolane, oxaprozin, oxyphenbutazone, oxymetholone, paranyline hydrochloride, pentosan polysulfate sodium, phenbutazone sodium glycerite, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, stanozolol, sudoxicam, sulindac, suprofen, talmetacin, talniflumate, talosalate, tebufelone, tenidap, tenidap sodium, tenoxicam, tesicam, tesimide, testosterone, testosterone blends, tetrydamine, tiopinac, tixocortol pivalate, tolmetin, tolmetin sodium, triclonide, triflumidate, zidometacin, and zomepirac sodium.

In some embodiments of the invention, the pharmacological agent comprises a statin, i.e. a HMG-CoA reductase inhibitor. According to the invention, suitable statins include, without limitation, atorvastatin (Lipitor®), cerivastatin, fluvastatin (Lescol®), lovastatin (Mevacor®, Altocor®, Altoprev®), mevastatin, pitavastatin (Livalo®, Pitava®), pravastatin (Pravachol®, Selektine®, Lipostat®), rosuvastatin (Crestor®), and simvastatin (Zocor®, Lipex®). Several actives comprising a combination of a statin and another agent, such as ezetimbe/simvastatin (Vytorin®), are also suitable.

As set forth in Co-pending application Ser. No. 13/782,115, Applicant has found that the noted statins exhibit numerous beneficial properties that provide several beneficial biochemical actions or activities.

According to the invention, the biologically active and pharmacological agents referenced above can comprise any form. In some embodiments of the invention, the agents, e.g. simvastatin, comprise microcapsules that provide delayed delivery of the agent contained therein.

Referring now to FIG. 1, there is shown a depiction of a normal human heart 100. The heart wall 102 consists of an inner layer of simple squamous epithelium, referred to as the endocardium. The endocardium overlays the myocardium (a variably thick heart muscle) and is enveloped within a multi-layer tissue structure referred to as the pericardium. The innermost layer of the pericardium, referred to as the visceral pericardium or epicardium, covers the myocardium. An outermost layer of the pericardium, referred to as the fibrous pericardium, attaches the parietal pericardium to the sternum, the great vessels and the diaphragm.

Figure 2:
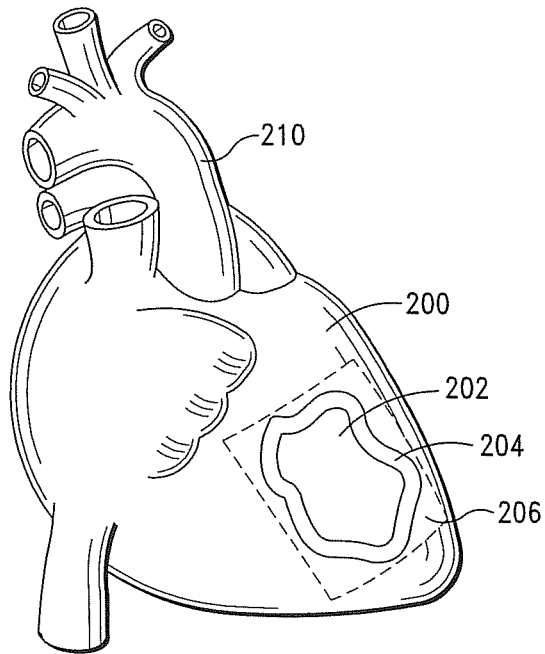
FIG. 2 is a of a heart having an ischemic infracted region.

Referring now to FIG. 2, there is shown a depiction of a heart 200 having an ischemic infarcted region 202, and a peri-infarcted region 204 that is surrounded by healthy non-ischemic myocardium tissue 206.

As indicated above, the ischemic infarcted region 202 (or myocardial infarction) can, and in many instances will trigger a cascading sequence of myocellular events. In many instances, the myocellular events lead to deterioration in ventricular function and heart failure.

As discussed in detail in Co-pending application Ser. No. 13/573,569, the effects of an ischemic infarcted region can be ameliorated or eliminated by delivering an ECM based composition of the invention directly to the infarcted cardiovascular tissue. In most instances, the ECM based compositions will induce neovascularization, host tissue proliferation, bioremodeling, and regeneration of new cardiac tissue structures with site-specific structural and functional properties.

According to the invention, the ECM based compositions can be delivered to infarcted cardiovascular tissue, as well as other damaged or diseased biological tissue, by various conventional means. In some embodiments, a multi-needle injection system, such as disclosed in U.S. Application No. 61/704,634, filed Sep. 24, 2012 and illustrated in FIGS. 3A and 3B is employed to deliver one or more ECM based compositions to damaged or diseased cardiovascular tissue.

Without departing from the spirit and scope of this invention, one of ordinary skill can make various changes and modifications to the invention to adapt it to various usages and conditions. As such, these changes and modifications are properly, equitably, and intended to be, within the full range of equivalence of the following claims.

What is claimed is:

1. A composition for treating damaged cardiovascular tissue, comprising:
    an extracellular matrix (ECM) composition consisting of acellular ECM from basement membrane of amniotic membrane and a combination of exogenously added growth factors selected from the group consisting of vascular endothelial growth factor (VEGF) and basic fibroblast growth factor (bFGF) or transforming growth factor beta (TGF-β), wherein a growth factor augmented ECM composition is formed, whereby, when said growth factor augmented ECM composition is delivered to infarcted cardiovascular tissue, said growth factor augmented ECM composition induces angiogenesis, bioremodeling of said infarcted cardiovascular tissue and regeneration of new cardiovascular tissue structures with site-specific structural and functional properties.

2. A method for treating a cardiovascular disorder, comprising the steps of:
    providing the extracellular matrix (ECM) composition according to claim 1; and
    administering said ECM composition to infarcted cardiovascular tissue associated with said cardiovascular disorder.

* * * * *